(12) United States Patent
Conrad et al.

(10) Patent No.: US 11,634,844 B2
(45) Date of Patent: Apr. 25, 2023

(54) CD EXTENSIBLE NONWOVEN COMPOSITE

(71) Applicant: Kimberly-Clark Worldwide, Inc., Neenah, WI (US)

(72) Inventors: John H. Conrad, Alpharetta, GA (US); James R. Fitts, Jr., Gainesville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 285 days.

(21) Appl. No.: 15/517,543

(22) PCT Filed: Dec. 10, 2015

(86) PCT No.: PCT/US2015/064868
§ 371 (c)(1),
(2) Date: Apr. 7, 2017

(87) PCT Pub. No.: WO2016/100054
PCT Pub. Date: Jun. 23, 2016

(65) Prior Publication Data
US 2017/0306536 A1    Oct. 26, 2017

Related U.S. Application Data

(60) Provisional application No. 62/094,378, filed on Dec. 19, 2014.

(51) Int. Cl.
*D04H 1/4291* (2012.01)
*B32B 27/12* (2006.01)
(Continued)

(52) U.S. Cl.
CPC ..... *D04H 1/4291* (2013.01); *A61F 13/15699* (2013.01); *A61F 13/49019* (2013.01);
(Continued)

(58) Field of Classification Search
USPC ........................................ 442/394, 195, 198
See application file for complete search history.

(56) References Cited

U.S. PATENT DOCUMENTS

| 3,338,992 A | 8/1967 | Kinney |
| 3,341,394 A | 9/1967 | Kinney |

(Continued)

FOREIGN PATENT DOCUMENTS

| WO | WO 00/28122 A1 | 5/2000 |
| WO | WO 03/089713 A1 | 10/2003 |

(Continued)

OTHER PUBLICATIONS

International Search Report and Written Opinion for PCT/US2015/064868 dated Mar. 31, 2016, 14 pages.

(Continued)

*Primary Examiner* — Lynda Salvatore
(74) *Attorney, Agent, or Firm* — Dority & Manning, P.A.

(57) ABSTRACT

A nonwoven composite that has a dimension in a machine direction and a cross-machine direction is provided. The composite comprises a nonwoven facing positioned adjacent to an elastic film. The nonwoven facing contains a spunbond web that is formed by necking a base spunbond web. The base spunbond web includes a plurality of fibers generally oriented in the machine direction and exhibiting a machine direction tensile strength and cross-machine direction tensile strength. The ratio of the machine direction tensile strength to the cross-machine direction tensile strength is about 4:1 or more.

14 Claims, 3 Drawing Sheets

(51) Int. Cl.

| | | |
|---|---|---|
| B32B 5/02 | (2006.01) | |
| B32B 27/32 | (2006.01) | |
| D04H 3/04 | (2012.01) | |
| B32B 5/08 | (2006.01) | |
| B32B 7/14 | (2006.01) | |
| B32B 27/00 | (2006.01) | |
| A61F 13/15 | (2006.01) | |
| A61F 13/49 | (2006.01) | |
| A61L 15/24 | (2006.01) | |
| B32B 7/12 | (2006.01) | |
| D04H 1/593 | (2012.01) | |
| A61F 13/51 | (2006.01) | |

(52) U.S. Cl.
CPC .............. *A61L 15/24* (2013.01); *B32B 5/022* (2013.01); *B32B 5/08* (2013.01); *B32B 7/12* (2013.01); *B32B 7/14* (2013.01); *B32B 27/00* (2013.01); *B32B 27/12* (2013.01); *B32B 27/32* (2013.01); *D04H 1/593* (2013.01); *D04H 3/04* (2013.01); *A61F 13/51* (2013.01); *A61F 2013/49022* (2013.01); *B32B 2262/0253* (2013.01); *B32B 2262/12* (2013.01); *B32B 2307/51* (2013.01); *B32B 2307/54* (2013.01); *B32B 2555/00* (2013.01); *B32B 2555/02* (2013.01)

(56) References Cited

U.S. PATENT DOCUMENTS

| | | | |
|---|---|---|---|
| 3,354,506 | A | 11/1967 | Raley |
| 3,485,706 | A | 12/1969 | Evans |
| 3,502,538 | A | 3/1970 | Petersen |
| 3,502,763 | A | 3/1970 | Hartmann |
| 3,542,615 | A | 11/1970 | Dobo et al. |
| 3,650,649 | A | 3/1972 | Schippers |
| 3,692,618 | A | 9/1972 | Dorschner et al. |
| 3,801,429 | A | 4/1974 | Schrenk et al. |
| 3,802,817 | A | 4/1974 | Matsuki et al. |
| 3,849,241 | A | 11/1974 | Butin et al. |
| 3,855,046 | A | 12/1974 | Hansen et al. |
| 3,949,128 | A | 4/1976 | Ostermeier |
| 4,041,203 | A | 8/1977 | Brock et al. |
| 4,323,534 | A | 4/1982 | DesMarais |
| 4,340,563 | A | 7/1982 | Appel et al. |
| 4,374,888 | A | 2/1983 | Bornslaeger |
| 4,663,220 | A | 5/1987 | Wisneski et al. |
| 4,704,116 | A | 11/1987 | Enloe |
| 4,766,029 | A | 8/1988 | Brock et al. |
| 4,789,592 | A | 12/1988 | Taniguchi et al. |
| 4,795,668 | A | 1/1989 | Krueger et al. |
| 4,798,603 | A | 1/1989 | Meyer et al. |
| 4,834,738 | A | 5/1989 | Kielpikowski et al. |
| 4,886,512 | A | 12/1989 | Damico et al. |
| 4,940,464 | A | 7/1990 | Van Gompel et al. |
| 4,965,122 | A | 10/1990 | Morman |
| 4,981,747 | A | 1/1991 | Morman |
| 5,057,368 | A | 10/1991 | Largman et al. |
| 5,069,970 | A | 12/1991 | Largman et al. |
| 5,093,422 | A | 3/1992 | Himes |
| 5,108,820 | A | 4/1992 | Kaneko et al. |
| 5,162,074 | A | 11/1992 | Hills |
| 5,169,706 | A | 12/1992 | Collier, IV et al. |
| 5,176,668 | A | 1/1993 | Bernardin |
| 5,176,672 | A | 1/1993 | Bruemmer et al. |
| 5,192,606 | A | 3/1993 | Proxmire et al. |
| 5,213,881 | A | 5/1993 | Timmons et al. |
| 5,226,992 | A | 7/1993 | Morman |
| 5,272,236 | A | 12/1993 | Lai et al. |
| 5,277,976 | A | 1/1994 | Hogle et al. |
| 5,304,599 | A | 4/1994 | Himes |
| 5,322,728 | A | 6/1994 | Davey et al. |
| 5,332,613 | A | 7/1994 | Taylor et al. |
| 5,336,545 | A | 8/1994 | Morman |
| 5,336,552 | A | 8/1994 | Strack et al. |
| 5,366,793 | A | 11/1994 | Fitts, Jr. et al. |
| 5,382,400 | A | 1/1995 | Pike et al. |
| 5,464,688 | A | 11/1995 | Timmons et al. |
| 5,466,410 | A | 11/1995 | Hills |
| 5,472,775 | A | 12/1995 | Obijeski et al. |
| 5,486,166 | A | 1/1996 | Bishop et al. |
| 5,490,846 | A | 2/1996 | Ellis et al. |
| 5,509,915 | A | 4/1996 | Hanson et al. |
| 5,539,056 | A | 7/1996 | Yang et al. |
| 5,558,659 | A | 9/1996 | Sherrod et al. |
| D375,844 | S | 11/1996 | Edwards et al. |
| 5,571,619 | A | 11/1996 | McAlpin et al. |
| 5,596,052 | A | 1/1997 | Resconi et al. |
| 5,620,779 | A | 4/1997 | Levy et al. |
| 5,649,916 | A | 7/1997 | DiPalma et al. |
| D390,708 | S | 2/1998 | Brown |
| 5,766,389 | A | 6/1998 | Brandon et al. |
| 5,914,084 | A | 6/1999 | Benson et al. |
| 5,932,497 | A | 8/1999 | Morman et al. |
| 5,962,112 | A | 10/1999 | Haynes et al. |
| 5,964,742 | A | 10/1999 | McCormack et al. |
| 5,997,981 | A | 12/1999 | McCormack et al. |
| 6,015,764 | A | 1/2000 | McCormack et al. |
| D428,267 | S | 7/2000 | Romano, III et al. |
| 6,090,325 | A | 7/2000 | Wheat et al. |
| 6,093,665 | A | 7/2000 | Sayovitz et al. |
| 6,110,158 | A | 8/2000 | Kielpikowski |
| 6,111,163 | A | 8/2000 | McCormack et al. |
| 6,114,263 | A | 9/2000 | Benson et al. |
| 6,200,669 | B1 | 3/2001 | Marmon et al. |
| 6,331,268 | B1 | 12/2001 | Kauschke et al. |
| 6,383,431 | B1 | 5/2002 | Dobrin et al. |
| 6,461,457 | B1 | 10/2002 | Taylor et al. |
| 6,500,563 | B1 | 12/2002 | Datta et al. |
| 6,511,465 | B1 | 1/2003 | Freiburger et al. |
| 6,524,521 | B1 | 2/2003 | Kuroiwa et al. |
| 6,645,190 | B1 | 11/2003 | Olson et al. |
| 6,663,611 | B2 | 12/2003 | Blaney et al. |
| 6,761,711 | B1 | 7/2004 | Fletcher et al. |
| 6,824,734 | B2 | 11/2004 | Boggs et al. |
| 6,888,044 | B2 | 5/2005 | Fell et al. |
| 7,172,398 | B2 | 2/2007 | Bentley et al. |
| 7,320,948 | B2 | 1/2008 | Morman et al. |
| 8,067,318 | B2 | 11/2011 | Martin |
| 2002/0105110 | A1 | 8/2002 | Dobrin et al. |
| 2003/0100238 | A1* | 5/2003 | Morman .................... B32B 5/26 442/328 |
| 2003/0157859 | A1* | 8/2003 | Ishikawa ................. A61F 13/51 442/382 |
| 2004/0060112 | A1 | 4/2004 | Fell et al. |
| 2004/0102125 | A1* | 5/2004 | Morman ............... B32B 37/065 442/394 |
| 2004/0110442 | A1 | 6/2004 | Rhim et al. |
| 2005/0245162 | A1 | 11/2005 | McCormack et al. |
| 2006/0003656 | A1 | 1/2006 | Morman |
| 2006/0151914 | A1 | 7/2006 | Gerndt et al. |
| 2007/0254545 | A1 | 11/2007 | Martin |
| 2011/0143623 | A1 | 6/2011 | Abed et al. |
| 2012/0208422 | A1 | 8/2012 | Koori et al. |
| 2016/0251788 | A1* | 9/2016 | Huang ..................... B32B 5/08 442/382 |

FOREIGN PATENT DOCUMENTS

| | | |
|---|---|---|
| WO | WO 03/089714 A1 | 10/2003 |
| WO | WO 2007/106088 A1 | 9/2007 |

OTHER PUBLICATIONS

Supplementary European Search Report dated Aug. 1, 2018, 8 pages.

* cited by examiner

CD EXTENSIBLE NONWOVEN COMPOSITE

RELATED APPLICATION

The present application is the national stage entry of International Patent Application No. PCT/US2015/064868 having a filing date of Dec. 10, 2015, which claims priority to U.S. Patent Application Serial No. 62/094,378 filed on Dec. 19, 2014, which are incorporated herein in their entirety by reference thereto.

BACKGROUND OF THE INVENTION

Stretchable nonwoven composites are generally formed from a nonwoven web facing and an elastic layer (film, strands and/or fibrous structure) and used in a variety of products, such as disposable diapers and other personal hygiene products. Some laminates of this type are made with necked spunbond facings and are stretchable in the cross-machine direction. Unfortunately, these materials tend to require a too high of a force to extend the laminate during use of the product. Various solutions have been proposed to this problem. For example, intermeshing grooved rolls or discs have been used to stretch composites and create some degree of low force extensibility in the cross-machine direction. However, this approach can be costly and result in damage to the nonwoven web facing. As such, a need currently exists for a nonwoven composite that provides good extension at low force in the cross-machine direction.

SUMMARY OF THE INVENTION

In accordance with one embodiment of the present invention, a nonwoven composite is disclosed that has a dimension in a machine direction and a cross-machine direction. The nonwoven composite comprises a nonwoven facing positioned adjacent to an elastic film. The nonwoven facing contains a necked spunbond web formed from a plurality of fibers that are generally oriented in the machine-direction. The composite has a peak elongation in the cross-machine direction of about 100% or more and experiences a load at 100% elongation in the cross-machine direction of about 450 grams-force per inch or less.

In accordance with another embodiment of the present invention, a method for forming a nonwoven facing that has a dimension in a machine direction and cross-machine direction is disclosed. The method comprises necking a base spunbond web so that a dimension of the web is reduced in the cross-machine direction. The base spunbond web has a machine direction tensile strength and cross-machine direction tensile strength, the ratio of the machine direction tensile strength to the cross-machine direction tensile strength being about 4:1 or more.

Other features and aspects of the present invention are described in more detail below.

BRIEF DESCRIPTION OF THE DRAWING

A full and enabling disclosure of the present invention, including the best mode thereof, directed to one of ordinary skill in the art, is set forth more particularly in the remainder of the specification, which makes reference to the appended figure in which.

Figure 1:
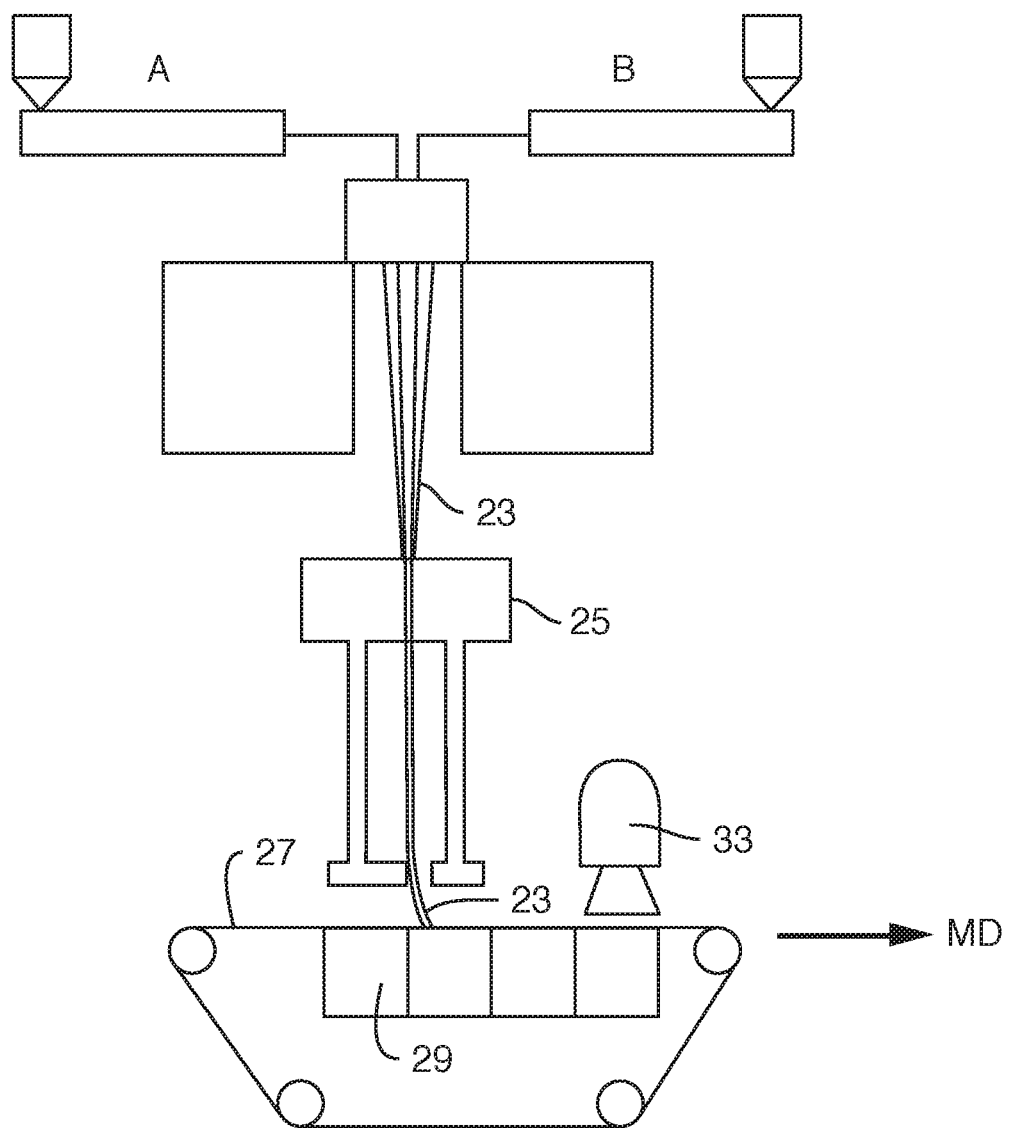
FIG. 1 is a schematic illustration of one embodiment of a method for forming a spunbond web for use in the present invention.

Repeat use of reference characters in the present specification and drawing is intended to represent same or analogous features or elements of the invention.

DETAILED DESCRIPTION OF REPRESENTATIVE EMBODIMENTS

Definitions

As used herein, the term "fibers" generally refer to elongated extrudates that may be formed by passing a polymer through a forming orifice, such as a die. Unless noted otherwise, the term "fibers" includes discontinuous fibers having a definite length (e.g., stable fibers) and substantially continuous filaments. Substantially filaments may, for instance, have a length much greater than their diameter, such as a length to diameter ratio ("aspect ratio") greater than about 15,000 to 1, and in some cases, greater than about 50,000 to 1.

As used herein the term "nonwoven web" generally refers to a web having a structure of fibers that are interlaid, but not in an identifiable manner as in a knitted fabric. Examples of suitable nonwoven webs include, but are not limited to, meltblown webs, spunbond webs, bonded carded webs, airlaid webs, coform webs, hydraulically entangled webs, and so forth.

As used herein, the term "spunbond" web generally refers to a nonwoven web containing substantially continuous filaments formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al.

As used herein, the term "meltblown" web or facing generally refers to a nonwoven web containing fibers formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al.

As used herein, the terms "machine direction" or "MD" generally refers to the direction in which a material is produced. The term "cross-machine direction" or "CD" generally refers to the direction perpendicular to the machine direction. Dimensions measured in the cross-machine direction are also referred to as "width" dimension, while dimensions measured in the machine direction are referred to as "length" dimensions.

As used herein the term "extensible" generally refers to a material that stretches or extends in the direction of an applied force (e.g., CD or MD direction) by about 50% or more, in some embodiments about 75% or more, in some embodiments about 100% or more, and in some embodiments, about 200% or more of its relaxed length or width.

As used herein, the term "elastic" generally refers to an extensible material that, upon application of a stretching force, is stretchable in at least one direction (e.g., CD or MD direction), and which upon release of the stretching force, contracts/returns to approximately its original dimension. For example, the stretched material may contract or recover at least about 50%, and even more desirably, at least about 80% of its stretched length. It should be understood that an extensible material may lack recovery properties such that it is considered an "inelastic" material. Materials may be tested for elastic properties using a cyclical testing procedure, such as described below.

Detailed Description

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a composite that contains a nonwoven facing positioned adjacent to an elastic film. The nonwoven facing contains at least one spunbond web that is formed by necking a base spunbond web. The base spunbond web includes a plurality of fibers generally oriented in the machine direction. Of course, all of the fibers need not extend in the machine direction. In fact, the fibers may be entangled with each other such that a portion of the fibers are positioned at an angle relative to the machine direction. Nevertheless, the degree of machine direction orientation is such that the base spunbond web has a relatively high ultimate tensile strength (maximum load to break) in the machine direction ("MD tensile strength") as compared to its ultimate tensile strength in the cross-machine direction ("CD tensile strength"). Namely, the ratio of the MD tensile strength to the CD tensile strength is about 4:1 or more, in some embodiments from about 5:1 to about 30:1, and in some embodiments, from about 6:1 to about 20:1. For example, the base spunbond web may have a MD tensile strength of about 400 grams-force per inch ("gf/in") or more, in some embodiments from about 800 to about 2000 gf/in, and in some embodiments, from about 1000 to about 1600 gf/in, and a CD tensile strength of about 60 gf/in or more, in some embodiments from about 80 to about 800 gf/in, and in some embodiments, from about 100 to about 500 gf/in.

The base spunbond web may also exhibit a peak elongation (percent elongation at its peak load) in the machine direction ("MD elongation") that is greater than the peak elongation in the cross-machine direction ("CD elongation"). For example, the ratio of the MD elongation to the CD elongation may be about 2:1 or more, in some embodiments from about 3:1 to about 30:1, and in some embodiments, from about 4:1 to about 20:1. For example, the base spunbond web may have a MD elongation of about 20% or more, in some embodiments from about 25 to about 60%, and in some embodiments, from about 30 to about 45%, and a CD elongation of about 40% or more, in some embodiments from about 60 to about 200%, and in some embodiments, from about 70 to about 100%.

Due to its unique properties, the present inventors have discovered that the base spunbond web can be necked to a substantial extent. That is, the "percent necking" may be about 50% or more, in some embodiments from about 60% to about 95%, and some embodiments, from about 65% to about 90%. As used herein, the term "percent necking" is generally determined by subtracting a dimension of the spunbond web in the cross-machine direction after necking by the dimension prior to necking, dividing this result by the dimension prior to necking, and then multiplying the quotient by 100. The necked cross-machine direction dimension of the spunbond web may, for example, 5 to about 70 centimeters, in some embodiments from about 10 to about 50 centimeters, and in some embodiments, from about 15 to about 30 centimeters, while the un-necked dimension may range from about 70 to about 300 centimeters, in some embodiments from about 75 to about 200 centimeters, and in some embodiments, from about 80 to about 150 centimeters.

The ability to achieve such a high degree of necking can allow the web to be laminated to an elastic film to achieve a composite having excellent extensibility in the cross-machine direction. That is, the composite may exhibit a relatively high elongation at peak load ("peak elongation") in the cross-machine direction, such as about 100% or more, in some embodiments about 120% or more, and in some embodiments, from about 150% to about 500% in the cross-machine direction. The composite may, of course, also exhibit an elongation at peak load ("peak elongation") in the machine direction of about 50% or more, in some embodiments about 75% or more, and in some embodiments, from about 100% to about 500%. While possessing good extensibility in the cross-machine direction, the composite nevertheless may have a relatively low degree of cross-machine direction tension. This may be characterized by a relatively low load at 100% elongation in the cross-machine direction, such as about 450 gf/in or less, in some embodiments about 400 gf/in or less, and in some embodiments, from about 200 to about 400 gf/in. The percent load loss in the cross-machine direction may likewise be about 60% or less, in some embodiments about 55% or less, and in some embodiments, from about 20% to about 50%. The composite may also be elastic in the machine and/or cross-machine directions in that it is extensible in at least one direction upon application of the stretching force and, upon release of the stretching force, contracts/returns to approximately its original dimension. Desirably, the composite contracts or recovers at least 50%, and even more desirably, at least 80% of the stretched dimension in the MD and/or CD directions. In this regard, various embodiments of the present invention will now be described in more detail.

I. Nonwoven Facing

As noted above, the nonwoven facing contains at least one spunbond web that is formed by necking a base spunbond web. The web includes a plurality of fibers generally oriented in the machine direction. The fibers may have any of a variety of different configuration as is known in the art. For example, monocomponent and/or multicomponent fibers may be employed. Monocomponent fibers, for instance, are typically formed by extruding a polymer composition from a single extruder. Multicomponent fibers, on the other hand, are generally formed from two or more polymer compositions (e.g., bicomponent fibers) extruded from separate extruders. The polymer compositions may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, 5,069,970 to Largman, et al., and U.S. Pat. No. 5,057,368 to Largman, et al.

Regardless of the particular configuration employed, it is typically desired that the fibers have a relatively low modulus. Among other things, the present inventors have discovered that such fibers can be more easily oriented in the machine direction as they are formed. Polymers for use in forming such fibers typically have a modulus of about 800 MPa or less, in some embodiments about 750 MPa or less, and in some embodiments, from about 1 to about 700 MPa, as determined in accordance with ASTMD638-10. Any of a variety of low modulus polymers may generally be employed. In one embodiment, for example, the low modulus polymer composition may contain an ethylene polymer having a modulus of elasticity of from about 50 to about 700 MPa, in some embodiments from about 75 to about 600 MPa, and in some embodiments, from about 100 to about 500 MPa, as determined in accordance with ASTM D638-10. The ethylene polymer may also have a melt flow index of from about 1 to about 100 grams per 10 minutes, in some embodiments from about 5 to about 50 grams per 10 minutes, and in some embodiments, from about 10 to about 40 grams per 10 minutes, determined at a load of 2160 grams and at 190° C., as determined in accordance with ASTM D1238-13 (or ISO 1133). The melting temperature of the ethylene polymer may also be from about 50° C. to about 145° C., in some embodiments from about 75° C. to about 140° C., and in some embodiments, from about 100° C. to about 135° C.

Any of a variety of ethylene polymers may generally be employed in the present invention. In one embodiment, for instance, the ethylene polymer may be a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %. The density of the polyethylene may vary depending on the type of polymer employed, but generally ranges from about 0.85 to about 0.96 grams per cubic centimeter ($g/cm^3$). Polyethylene "plastomers", for instance, may have a density in the range of from about 0.85 to about 0.91 $g/cm^3$. Likewise, "linear low density polyethylene" (LLDPE) may have a density in the range of from about 0.91 to about 0.940 $g/cm^3$; "low density polyethylene" (LDPE) may have a density in the range of from about 0.910 to about 0.940 $g/cm^3$; and "high density polyethylene" (HDPE) may have density in the range of from about 0.940 to about 0.960 $g/cm^3$, such as determined in accordance with ASTM 1505-10. LLDPE may be particularly suitable for use in the first polyolefin composition.

Any of a variety of known techniques may generally be employed to form the ethylene polymer. For instance, olefin polymers may be formed using a free radical or a coordination catalyst (e.g., Ziegler-Natta). Typically, the ethylene polymer is formed from a single-site coordination catalyst, such as a metallocene catalyst. Such a catalyst system produces ethylene polymers in which a comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obiieski et al.; U.S. Pat. No. 5,272,236 to Lai et al.; and U.S. Pat. No. 6,090,325 to Wheat, et al. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

Another example of a suitable low modulus polymer is a ductile propylene polymer. The modulus of elasticity of the ductile propylene polymer may, for instance, range from about 1 to about 500 MPa, in some embodiments from about 5 to about 300 MPa, and in some embodiments, from about 10 to about 100 MPa, as determined in accordance with ASTM D638-10. The ductile propylene polymer may also have a relatively low melt flow index, such as from about 15 to about 1,000 grams per 10 minutes, in some embodiments from about 20 to about 500 grams per 10 minutes, and in some embodiments, from about 25 to about 200 grams per 10 minutes, determined at a load of 2160 grams and at 230° C., as determined in accordance with ASTM D1238-13 (or ISO 1133). Of course, in other embodiments, polymers with a relatively high melt flow index may be employed, such as from about 1,000 to about 5,000 grams per 10 minutes, in some embodiments from about 1,500 to about 4,000 grams per 10 minutes, and in some embodiments, from about 1,600 to about 3,000 grams per 10 minutes, determined at a load of 2160 grams and at 230° C., as determined in accordance with ASTM D1238-13(or ISO 1133). In addition, the ductile propylene polymer may also have a relatively low melting point and a relatively low degree of crystallinity. For example, the melting temperature of the ductile polymer may be from about 40° C. to about 120° C., in some embodiments from about 50° C. to about 100° C., and in some embodiments, from about 55° C. to about 85° C. Likewise, the degree of crystallinity of the polymer may be from about 1% to about 35%, in some embodiments from about 3% to about 20%, and in some embodiments, from about 5% and about 25%.

Any of a variety of ductile propylene polymers having the characteristics noted above may generally be employed in the present invention. In one particular embodiment, for instance, the propylene polymer is a low crystalline homopolymer or copolymer (e.g., random or block) containing about 10 wt. % or less of co-monomers (e.g., α-olefins), and in some embodiments, about 2 wt. % or less. Such polymers are typically formed using a metallocene catalyst, either alone or in combination with a small amount of an α-olefin co-monomer. Some examples of suitable metallocene catalysts are described above. Other examples of suitable metallocene catalysts for low crystalline propylene polymers may be described in U.S. Patent Publication No. 2012/0208422 to Koori, et al. For instance, such metallocene catalysts may be obtained from a combination of a promoter and a transition metal compound that form a cross-linked structure via two cross-linking groups. Suitable promoters may include, for instance, dimethylanilinium tetrakis(pentafluorophenyl)borate, triethylammonium tetraphenylborate, tri(n-butyl)ammonium tetraphenylborate, trimethylammonium tetraphenylborate, tetraethylammonium tetraphenylborate, methyl(tri-n-butyl)ammonium tetraphenylborate, benzyl(tri-n-butyl)ammonium tetraphenylborate, aluminoxane (e.g., methylaluminoxane, ethylaluminoxane, isobutylaluminoxane, etc.), and so forth. Suitable transition metal compounds may likewise include (1,2'-dimethylsilylene)(2,1'-dimethylsilylene)bis(3-n-butyl-indenyl)zirconium dichloride, (1,2'-dimethylsilylene) (2,1'-dimethylsilylene)bis(3-trimethylsilylmethylindenyl)zirconium dichloride, (1,2'-dimethylsilylene)(2,1'-dimethylsilylene)bis(3-phenylindenyl)zirconium dichloride, (1,2'-dimethylsilylene)(2,1'-dimethylsilylene)bis(4,5-benzo-indenyl)zirconium dichloride, (1,2'-dimethylsilylene)(2,1'-dimethylsilylene)bis(4-isopropylindenyl)zirconium dichloride, (1,2'-dimethylsilylene)(2,1'-dimethylsilylene)bis(5,6-dimethylindenyl)zirconium dichloride, (1,2'-dimethylsilylene)(2,1'-dimethylsilylene)bis(4,7-di-isopropylindenyl)zirconium dichloride, (1,2'-dimethylsilylene)(2,1'-dimethylsilylene)bis(4-phenylindenyl)zirconium dichloride, (1,2'-dimethylsilylene) (2,1'-dimethylsilylene)bis(3-methyl-4-isopropylindenyl) zirconium dichloride, (1,2'-dimethylsilylene)(2,1'-dimethylsilylene)bis(5,6-benzoindenyl)zirconium dichloride, (1,2'-dimethylsilylene)(2,1'-isopropylidene)-bis (indenyl)zirconium dichloride, (1,2'-dimethylsilylene)(2,1'-isopropylidene)-bis(3-methylindenyl)zirconium dichloride, (1,2'-dimethylsilylene)(2,1'-isopropylidene)-bis(3-isopropylindenyl)zirconium dichloride, (1,2'-dimethylsilylene)(2,1'-isopropylidene)-bis(3-n-butylindenyl)zirconium dichloride, and (1,2'-dimethylsilylene)(2,1'-isopropylidene)-bis(3-trimethylsilylmethylin-denyl)zirconium dichloride, etc., as well as transition metal compounds produced by substituting zirconium in the aforementioned compounds with titanium or hafnium.

The ductile propylene polymer typically has a density in the range of from 0.85 to 0.91 g/cm$^3$, and in some embodiments, from about 0.85 to 0.089 g/cm$^3$, such as determined in accordance with ASTM 1505-10. The ductile propylene polymer may also have a weight average molecular weight of from about 10,000 to about 200,000 grams per mole, in some embodiments from about 30,000 to about 100,000 grams per mole, and in some embodiments, from about 40,000 to about 80,000 grams per mole, as well as a polydispersity index (weight average molecular weight divided by number average molecular weight) of about 4 or less, and in some embodiments, about 3 or less. Commercially available examples of such metallocene-catalyzed propylene polymers may include, for instance, L-MODU™ S901, S600 or S400, which are available from Idemitsu Kosan.

Yet another example of a low modulus polymer that can be employed is an olefinic elastomer, such as a copolymer of propylene and an α-olefin. Suitable α-olefins may be linear or branched (e.g., one or more $C_1$-$C_3$ alkyl branches, or an aryl group) and formed from olefins, such as $C_2$-$C_{20}$ α-olefins, $C_2$-$C_{12}$ α-olefins, or $C_2$-$C_8$ αolefins. Specific examples include ethylene, butene; 3-methyl-1-butene; 3,3-dimethyl-1-butene; pentene; pentene with one or more methyl, ethyl or propyl substituents; hexene with one or more methyl, ethyl or propyl substituents; heptene with one or more methyl, ethyl or propyl substituents; octene with one or more methyl, ethyl or propyl substituents; nonene with one or more methyl, ethyl or propyl substituents; ethyl, methyl or dimethyl-substituted decene; dodecene; styrene; and so forth. Particularly desired α-olefin comonomers are ethylene, butene (e.g., 1-butene), hexene, and octene (e.g., 1-octene or 2-octene). The propylene content of the propylene/α-olefin copolymer is typically from about 60 mole % to about 99.5 mole %, in some embodiments from about 80 mole % to about 99 mole %, and in some embodiments, from about 85 mole % to about 98 mole %. The α-olefin content may likewise range from about 0.5 mole % to about 40 mole %, in some embodiments from about 1 mole % to about 20 mole %, and in some embodiments, from about 2 mole % to about 15 mole %. Generally speaking, the copolymer has a density lower than that of certain polyolefins (e.g., LLDPE), but approaching and/or overlapping that of other elastomers. For example, the density of the copolymer may be about 0.91 grams per cubic centimeter (g/cm$^3$) or less, in some embodiments from about 0.85 to about 0.89 g/cm$^3$, and in some embodiments, from about 0.85 g/cm.sup.3 to about 0.88 g/cm$^3$. Such propylene copolymers are commercially available under the designations VISTAMAXX™ from ExxonMobil Chemical Co. and VERSIFY™ available from Dow Chemical Co.

The particular manner in which the low modulus fiber is incorporated into the fibers of the present invention may vary. For example, the fibers may be monocomponent fibers that are formed from a low modulus polymer composition that includes only low modulus polymers or that includes a blend of low modulus polymers with other additives and/or polymers (e.g., rigid polymers). In one embodiment, for instance, the polymer composition of such fibers may contain a blend of a ductile polymer as described above (e.g., ductile propylene polymer) and a rigid polymer that has a modulus of elasticity of from about 800 to about 4,000 MPa, in some embodiments from about 1,000 to about 3,000 MPa, and in some embodiments, from about 1,200 to about 2,500 MPa, as determined in accordance with ASTM D638-10. Among other things, the rigid polymer that can provide good strength and durability to the resulting spunbond web. Rigid polymers may, for instance, constitute from about 80 wt. % to about 99.5 wt. %, in some embodiments from about 85 wt. % to about 99 wt. %, and in some embodiments, from about 90 wt. % to about 98 wt. % of the polymer composition. The ductile propylene polymers may likewise constitute from about 0.1 wt. % to about 15 wt. %, in some embodiments from about 0.5 wt. % to about 10 wt. %, and in some embodiments, from about 1 wt. % to 8 wt. % of the polymer composition.

Any of a variety of rigid polymers having the characteristics noted above may generally be employed. In one particular embodiment, for instance, the rigid polymer is a propylene polymer, such as an isotactic or syndiotactic homopolymer or copolymer (e.g., random or block) containing about 10 wt. % or less of co-monomers (e.g., α-olefins), and in some embodiments, about 2 wt. % or less. The term "syndiotactic" generally refers to a tacticity in which a substantial portion, if not all, of the methyl groups alternate on opposite sides along the polymer chain. On the other hand, the term "isotactic" generally refers to a tacticity in which a substantial portion, if not all, of the methyl groups are on the same side along the polymer chain. Such polymers are typically formed using a Ziegler-Natta catalyst, either alone or in combination with a small amount of an α-olefin co-monomer. Isotactic polymers, for instance, typically have a density in the range of from 0.88 to 0.94 g/cm$^3$, and in some embodiments, from about 0.89 to 0.91 g/cm$^3$, such as determined in accordance with ASTM 1505-10. Commercially available rigid propylene homopolymers may include, for instance, Metocene™ MF650Y and MF650X, which are available from Basell Polyolefins, as well as PP 3155, which is available from Exxon Mobil. Other examples of suitable propylene polymers may be described in U.S. Pat. No. 6,500,563 to Datta, et al.; U.S. Pat. No. 5,539,056 to Yanq, et al.; and U.S. Pat. No. 5,596,052 to Resconi, et al.

If desired, a fatty acid derivative may also be employed in the polymer composition, such as in a blend of ductile and rigid polymers, to help achieve the desired degree of ductility. Suitable fatty acid derivatives for use in the composition may include, for instance, fatty acid amides, fatty acid esters, fatty acid salts, and so forth. In one particular embodiment, for example, the fatty acid derivative may be a fatty acid amide. The fatty acid amide may be any suitable amide compound derived from the reaction between a fatty acid and ammonia or an amine-containing compound (e.g., a compound containing a primary amine group or a secondary amine group). The fatty acid may be any suitable fatty acid, such as a saturated or unsaturated $C_8$-$C_{28}$ fatty acid or a saturated or unsaturated $C_{12}$-$C_{28}$ fatty acid. In certain embodiments, the fatty acid may be erucic acid (i.e., cis-13-docosenoic acid), oleic acid (i.e., cis-9-octadecenoic acid), stearic acid (octadecanoic acid), behenic acid (i.e., docosanoic acid), arachic acid (i.e., arachidinic acid or eicosanoic acid), palmitic acid (i.e., hexadecanoic acid), and mixtures or combinations thereof. The amine-containing compound can be any suitable amine-containing compound, such as fatty amines (e.g., stearylamine or oleylamine), ethylenediamine, 2,2'-iminodiethanol, and 1,1'-iminodipropan-2-ol.

More particularly, the fatty acid amide may be a fatty acid amide having the structure of one of Formulae (I)-(V):

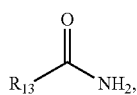
(I)

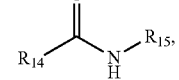
(II)

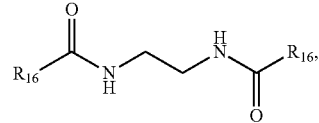
(III)

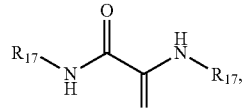
(IV)

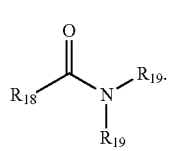
(V)

wherein, $R_{13}$, $R_{14}$, $R_{15}$, $R_{16}$, and $R_{18}$ are independently selected from $C_7$-$C_{27}$ alkyl groups and $C_7$-$C_{27}$ alkenyl groups, and in some embodiments, $C_{11}$-$C_{27}$ alkyl groups and $C_{11}$-$C_{27}$ alkenyl groups;

$R_{17}$ is selected from $C_8$-$C_{28}$ alkyl groups and $C_8$-$C_{28}$ alkenyl groups, and in some embodiments, $C_{12}$-$C_{28}$ alkyl groups and $C_{12}$-$C_{28}$ alkenyl groups; and $R_{19}$ is —$CH_2CH_2OH$ or —$CH_2CH(CH_3)OH$.

For example, the fatty acid amide may have the structure of Formula (I), where $R_{13}$ is —$CH_2(CH_2)_{10}CH$=$CH(CH_2)_7CH_3$(erucamide), —$CH_2(CH_2)_6CH$=$CH(CH_2)_7CH_3$(oleamide), —$CH_2(CH_2)_{15}CH_3$, —$CH_2(CH_2)_{19}CH_3$, or —$CH_2(CH_2)_{17}CH_3$. In other embodiments, the fatty acid amide may have the structure of Formula (II) where $R_{14}$ is —$CH_2(CH_2)_{10}CH$=$CH(CH_2)_7CH_3$ and $R_{15}$ is —$CH_2(CH_2)_{15}CH_3$, or where $R_{14}$ is —$CH_2(CH_2)_6CH$=$CH(CH_2)_7CH_3$ and $R_{15}$ is —$CH_2(CH_2)_{13}CH_3$. Likewise, in yet other embodiments, the fatty acid amide may have the structure of Formula (III) where $R_{16}$ is $CH_2(CH_2)_{15}CH_3$ or —$CH_2(CH_2)_6CH$=$CH(CH_2)_7CH_3$. The composition may also contain a mixture of two or more such fatty acid amides.

If desired, fatty acid esters may also be employed. Fatty acid esters may be obtained by oxidative bleaching of a crude natural wax and subsequent esterification of a fatty acid with an alcohol. The fatty acid may be a $C_8$-$C_{28}$ fatty acid or a saturated or unsaturated $C_{12}$-$C_{28}$ fatty acid, such as described above. The alcohol may have 1 to 4 hydroxyl groups and 2 to 20 carbon atoms. When the alcohol is multifunctional (e.g., 2 to 4 hydroxyl groups), a carbon atom number of 2 to 8 is particularly desired. Particularly suitable multifunctional alcohols may include dihydric alcohol (e.g., ethylene glycol, propylene glycol, butylene glycol, 1,3-propanediol, 1,4-butanediol, 1,6-hexanediol and 1,4-cyclohexanediol), trihydric alcohol (e.g., glycerol and trimethylolpropane), tetrahydric alcohols (e.g., pentaerythritol and erythritol), and so forth. Aromatic alcohols may also be suitable, such as o-, m-and p-tolylcarbinol, chlorobenzyl alcohol, bromobenzyl alcohol, 2,4-dimethylbenzyl alcohol, 3,5-dimethylbenzyl alcohol, 2,3,5-cumobenzyl alcohol, 3,4,5-trimethylbenzyl alcohol, p-cuminyl alcohol, 1,2-phthalyl alcohol, 1,3-bis(hydroxymethyl)benzene, 1,4-bis(hydroxymethyl)benzene, pseudocumenyl glycol, mesitylene glycol and mesitylene glycerol. Fatty acid salts may also be employed, such as those formed by saponification of a fatty acid to neutralize excess carboxylic acids and form a metal salt. Saponification may occur with a metal hydroxide, such as an alkali metal hydroxide (e.g., sodium hydroxide) or alkaline earth metal hydroxide (e.g., calcium hydroxide). The resulting fatty acid salt typically includes an alkali metal (e.g., sodium, potassium, lithium, etc.) or alkaline earth metal (e.g., calcium, magnesium, etc.).

Besides having a monocomponent configuration, the fibers of the present invention may also include multicomponent fibers that have at least one component formed from a low modulus polymer composition, which can include only low modulus polymers or a blend of low modulus polymers with other additives and/or polymers (e.g., rigid polymers). In one embodiment, for instance, the multicomponent fibers may contain a low modulus component (e.g., sheath) and a rigid component (e.g., sheath). The low modulus component can be formed from any of the ductile polymers noted above, such as an ethylene polymer. The rigid component can likewise be formed from a variety of different polymers, such as a rigid propylene polymer.

Regardless of the specific polymers employed, a variety of techniques may generally be employed to form the MD-oriented spunbond web of the present invention. For example, in one embodiment, the spunbond web may be formed by a spunbond process in which a polymer composition is fed to an extruder and extruded through a conduit to a spinneret. Spinnerets for extruding fibers are well known to those of skill in the art. For example, the spinneret may include a housing containing a spin pack having a plurality of plates stacked one on top of each other and having a pattern of openings arranged to create flow paths for the polymer composition. The spinneret may also have openings arranged in one or more rows that form a downwardly extruding curtain of fibers when the polymer composition is extruded therethrough. The process may also employ a quench blower positioned adjacent the curtain of fibers extending from the spinneret. Air from the quench air blower may quench the fibers as they are formed. A fiber draw unit or aspirator may also be positioned below the spinneret to receive the quenched fibers. Fiber draw units or aspirators for use in melt spinning polymers are well-known in the art. The fiber draw unit may include an elongate vertical passage through which the fibers are drawn by aspirating air entering from the sides of the passage and flowing downwardly through the passage. A heater or blower may supply aspirating air to the fiber draw unit, which draws the fibers and ambient air through the fiber draw unit.

Various aspects of the fiber forming process can be selectively controlled in the present invention to help achieve the desired degree of MD orientation. Referring to FIG. 1, for instance, one embodiment of a process for forming fibers that can be employed in the present invention is shown in more detail. Although by no means required, the process shown in FIG. 1 is configured to form bicomponent substantially continuous fibers having an A/B configuration. More particular, polymer compositions A and B are initially supplied to a fiber spinning apparatus 21 to form bicomponent fibers 23. Once formed, the fibers 23 are traversed through a fiber draw unit 25 and deposited on a moving forming wire 27. Deposition of the fibers is aided by an under-wire vacuum supplied by a suction box 29 that pulls down the fibers 23 onto the forming wire 27. The forming wire 27 is porous so that vertical air flow created by the suction box 29 can cause the fibers to lie down. In one embodiment of the present invention, the flow rate of this air flow can be kept relatively low to enhance the tendency of the fibers 23 to remain oriented in the MD direction. Alternatively, the suction box can contain sections that extend in the machine direction to disrupt the vertical air flow with at the point where the fibers are laid onto the moving web, thereby allowing the fibers to have a higher degree of orientation in the machine direction. One example of such a technique is described, for instance, in U.S. Pat. No. 6,331,268. Of course, other techniques may also be employed to help ensure that the fibers remain oriented in the machine direction. For example, deflector guide plates or other mechanical elements can be employed, such as described in U.S. Pat. Nos. 5,366,793 and 7,172,398. The direction of the air stream used to attenuate the fibers as they are formed can also be used to adjust to effect machine direction orientation, such as described in U.S. Pat. No. 6,524,521. Apart from process described above, other known techniques may also be employed to form the fibers. In one embodiment, for example, the fibers may be quenched after they are formed and then directly deposited onto a forming wire without first being drawn in the manner described above. In such embodiments, as described above, the flow rate of this air flow can be kept relatively low to enhance the tendency of the fibers to remain oriented in the MD direction.

Generally speaking, the resulting fibers have an average size (e.g., diameter) of about 100 micrometer or less, in some embodiments from about 0.1 microns to about 50 microns, and in some embodiments, from about 0.5 microns to about 40 microns. The fibers may likewise have a denier of about 6 or less, in some embodiments about 3 or less, and in some embodiments, from about 0.5 to about 1.5. In certain embodiments, the fibers may be in the form of substantially continuous filaments.

Referring again to FIG. 1, once the fibers 23 are formed, they may be heated by a diffuser 33, which can blow hot air onto the surface of the fibers to lightly bond them together for further processing. A hot air knife may also be employed as an alternative to the diffuser. Other techniques for providing integrity to the web may also be employed, such heated calender rolls. In any event, the resulting fibers may then be bonded to form a consolidated, coherent nonwoven web structure. Any suitable bonding technique may generally be employed in the present invention, such as adhesive or autogenous bonding (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with polymer composition used to form the fibers. Suitable autogenous bonding techniques may include ultrasonic bonding, thermal bonding, through-air bonding, and so forth. Thermal point bonding, for instance, typically employs a nip formed between two rolls, at least one of which is patterned. Ultrasonic bonding, on the other hand, typically employs a nip formed between a sonic horn and a patterned roll.

Regardless of the technique employed, the present inventors have discovered that selective control over the bonding pattern of the spunbond web can further improve the extensibility of the resulting composite in the cross-machine direction. That is, similar to the fibers, at least a portion of the bond regions in the pattern are generally oriented in the machine direction. The bond regions may, for example, define a longitudinal dimension that generally extends in the machine direction and a lateral dimension that generally extends in the cross-machine direction. Of course, it should be understood that the longitudinal dimension may be skewed relative to the machine direction to a small extent. For example, the bond regions can be oriented from about 0° to about 20°, in some embodiments from about 1° to about 15°, and in some embodiments, from about 2° to about 10° relative to the machine direction. The aspect ratio of these bond regions (the ratio of the longitudinal dimension to the lateral dimension) may range from about 2 to about 100, in some embodiments from about 4 to about 50, and in some embodiments, from about 5 to about 20. The longitudinal dimension may, for example, be from about 300 to about 5000 micrometers, in some embodiments from about 500 to about 4000 micrometers, and in some embodiments, from about 1000 to about 2000 micrometers, while the lateral dimension may be from about 20 to about 500 micrometers, in some embodiments from about 40 to about 200 micrometers, and in some embodiments, from about 50 to about 150 micrometers.

Figure 2:
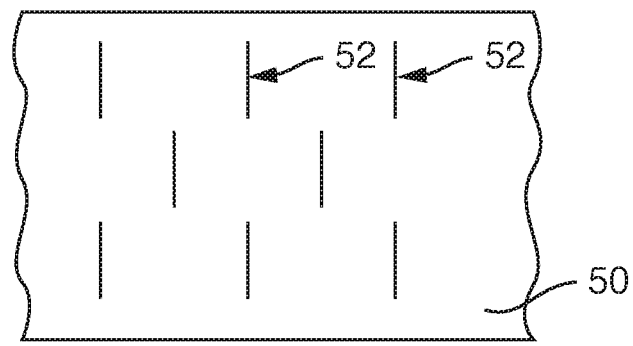
FIG. 2 illustrates one embodiment of a bonding pattern that may be employed in the present invention.
Figure 3:
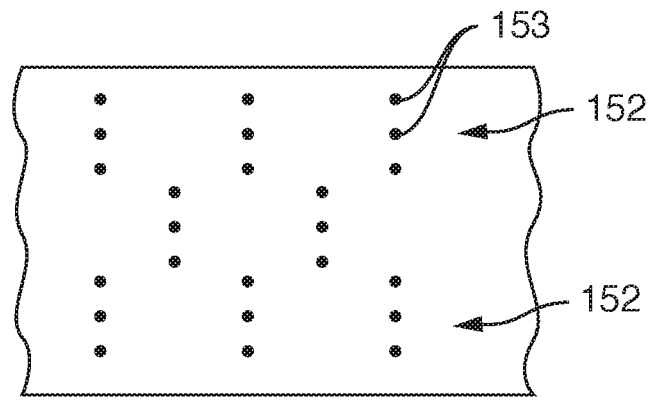
FIG. 3 illustrates another embodiment of a bonding pattern that may be employed in the present invention.
Figure 4:
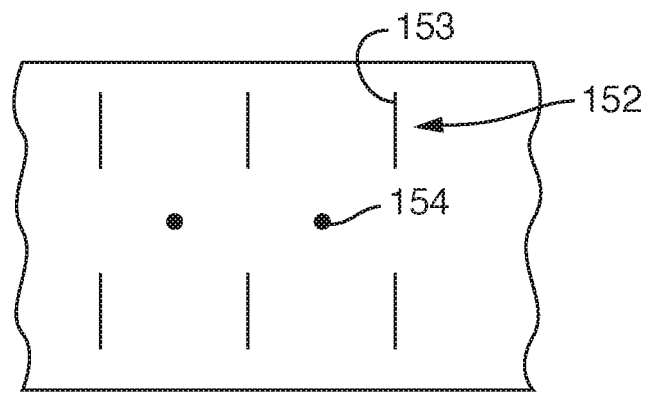
FIG. 4 illustrates yet another embodiment of a bonding pattern that may be employed in the present invention.

The particular nature of the bonding pattern can vary as desired. Referring to FIG. 2, for example, one embodiment of a spunbond web 50 is shown that contains a plurality of bond regions 52. The bond regions 52 are arranged in separate rows along the machine direction and spaced apart in the cross-machine direction within an individual row. The bond regions 52 of this particular embodiment are each in the form of continuous bond sites having an aspect ratio and MD orientation as noted above. However, this is by no means required. In FIG. 3, for instance, bond regions 152 are shown that are arranged in a pattern similar to that of FIG. 2, except that each region is formed from multiple bond sites 153 having a circular shape. While the individual bond sites 153 do not have the desired aspect ratio and MD orientation, they are nevertheless arranged together in a manner such that the overall bond region 152 possesses the same aspect ratio and MD orientation as the continuous bond sites of FIG. 2. It should also be understood that the bonding pattern can include additional bond sites that are not necessarily part of a MD-oriented bonding region. FIG. 4, for instance, illustrates an alternative embodiment in which additional bond sites 154 are provided that have a circular shape and do not form part of a MD-oriented bonding region. The pattern of the bond regions is also generally selected so that the spunbond web has a total bond area of less than about 50% (as determined by conventional optical microscopic methods), and in some embodiments, less than about 30%.

Once formed, the resulting base spunbond web is then necked to substantially reduce its dimension of in the cross-machine direction. Necking may occur prior to, during, and/or after lamination of the facing to the elastic film of the composite. Any of a variety of different necking techniques may be employed in the present invention as is well known in the art. Typically, the base spunbond web is stretched in the machine direction so that it is necked in the cross-machine direction. For example, such machine direction stretching may be accomplished by passing the spunbond web over a pair or series of necking rolls in which one or more downstream rolls operate at a faster speed than one or more upstream rolls. The ratio of the speed of the upstream rolls to the downstream rolls may, for example, range from about 0.70 to about 0.98, and in some embodiments, from about 0.75 to about 0.90. The difference in speed between the rolls can thus stretch the web to the desired extent. In one embodiment, for example, the rolls are arranged in an S-roll configuration. Examples of suitable necking techniques are described in U.S. Pat. Nos. 5,336, 545, 5,226,992, 4,981,747 and U.S. Pat. No. 4,965,122 to Morman, as well as U.S. Pat. No. 7,320,948 to Morman, et al. If desired, the spunbond web may be heated to facilitate the necking process.

The spunbond web may also be subjected to one or more additional post-treatment steps as is known in the art. For example, the spunbond web may be stretched in the cross-machine direction using known techniques, such as tenter frame stretching, groove roll stretching, etc. The spunbond web may also be subjected to other known processing steps, such as aperturing, heat treatments, etc. Regardless, the resulting necked spunbond web typically has a basis weight of from about 1 to about 45 grams per square meter or less, in some embodiments from about 2 to about 30 grams per square meter, and in some embodiments, from about 3 to about 20 grams per square meter.

The nonwoven facing of the composite may be formed entirely from the aforementioned necked spunbond web. Of course, it should also be understood that the nonwoven facing may contain additional layers (e.g., nonwoven webs, films, strands, etc.) if so desired. For example, the facing may contain two (2) or more layers, and in some embodiments, from three (3) to ten (10) layers (e.g., 3 or 5 layers). In one embodiment, for instance, the nonwoven facing may contain an inner nonwoven layer (e.g., meltblown or spunbond) positioned between two outer nonwoven layers (e.g., spunbond). For example, the inner nonwoven layer may be formed from the necked spunbond web of the present invention and one or both of the outer nonwoven layers may be formed from the necked spunbond web of the present invention or a conventional nonwoven web. Alternatively, the inner nonwoven layer may be formed from the necked spunbond web of the present invention or a conventional nonwoven web and one or both of the outer nonwoven layers may be formed from the necked spunbond web of the present invention. Various techniques for forming laminates of this nature are described in U.S. Pat. No. 4,041,203 to Brock et al.; U.S. Pat. No. 5,213,881 to Timmons. et al.; U.S. Pat. No. 5,464,688 to Timmons, et al.; U.S. Pat. No. 4,374, 888 to Bornslaeqer; U.S. Pat. No. 5,169,706 to Collier, et al.; and U.S. Pat. No. 4,766,029 to Brock et al. The facing may have other configurations and possess any desired number of layers, such as a spunbond-meltblown-meltblown-spunbond ("SMMS") laminate, spunbond-meltblown ("SM") laminate, etc.

II. Elastic Film

The elastic film of the composite may be formed from one or more elastomeric polymers that are melt-processable, i.e. thermoplastic. Any of a variety of thermoplastic elastomeric polymers may generally be employed in the present invention, such as elastomeric polyesters, elastomeric polyurethanes, elastomeric polyamides, elastomeric copolymers, elastomeric polyolefins, and so forth. In one particular embodiment, elastomeric semi-crystalline polyolefins are employed due to their unique combination of mechanical and elastomeric properties.

Semi-crystalline polyolefins have or are capable of exhibiting a substantially regular structure.

For example, semi-crystalline polyolefins may be substantially amorphous in their undeformed state, but form crystalline domains upon stretching. The degree of crystallinity of the olefin polymer may be from about 3% to about 30%, in some embodiments from about 5% to about 25%, and in some embodiments, from about 5% and about 15%. Likewise, the semi-crystalline polyolefin may have a latent heat of fusion ($\Delta H_f$), which is another indicator of the degree of crystallinity, of from about 15 to about 75 Joules per gram ("J/g"), in some embodiments from about 20 to about 65 J/g, and in some embodiments, from 25 to about 50 J/g. The semi-crystalline polyolefin may also have a Vicat softening temperature of from about 10° C. to about 100° C., in some embodiments from about 20° C. to about 80° C., and in some embodiments, from about 30° C. to about 60° C. The semi-crystalline polyolefin may have a melting temperature of from about 20° C. to about 120° C., in some embodiments from about 35° C. to about 90° C., and in some embodiments, from about 40° C. to about 80° C. The latent heat of fusion (ΔHf) and melting temperature may be determined using differential scanning calorimetry ("DSC") in accordance with ASTM D-3417 as is well known to those skilled in the art. The Vicat softening temperature may be determined in accordance with ASTM D-1525.

Exemplary semi-crystalline polyolefins include ethylene/α-olefin copolymers, propylene/α-olefin copolymers, etc., such as described in more detail above. Of course, other thermoplastic polymers may also be used to form the elastic film, either alone or in conjunction with the semi-crystalline polyolefins. For instance, a substantially amorphous block copolymer may be employed that has at least two blocks of a monoalkenyl arene polymer separated by at least one block of a saturated conjugated diene polymer. The monoalkenyl arene blocks may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene blocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth.

The amount of monoalkenyl arene (e.g., polystyrene) blocks may vary, but typically constitute from about 8 wt. % to about 55 wt. %, in some embodiments from about 10 wt. % to about 35 wt. %, and in some embodiments, from about 25 wt. % to about 35 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Particularly suitable thermoplastic elastomeric copolymers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copolymers include those sold under the brand names G 1652, G 1657, G 1730, MD6673, and MD6973. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene)("S-EP-S-EP") block copolymer.

The amount of elastomeric polymer(s) employed in the film may vary, but is typically about 30 wt. % or more of the film, in some embodiments about 50 wt. % or more, and in some embodiments, about 80 wt. % or more of the of the film. In one embodiment, for example, the semi-crystalline polyolefin(s) constitute about 70 wt. % or more of the film, in some embodiments about 80 wt. % or more of the film, and in some embodiments, about 90 wt. % or more of the film. In other embodiments, blends of semi-crystalline polyolefin(s) and elastomeric block copolymer(s) may be employed. In such embodiments, the block copolymer(s) may constitute from about 5 wt. % to about 50 wt. %, in some embodiments from about 10 wt. % to about 40 wt. %, and in some embodiments, from about 15 wt. % to about 35 wt. % of the blend. Likewise, the semi-crystalline polyolefin(s) may constitute from about 50 wt. % to about 95 wt. %, in some embodiments from about 60 wt. % to about 90 wt. %, and in some embodiments, from about 65 wt. % to about 85 wt. % of the blend. It should of course be understood that other elastomeric and/or non-elastomeric polymers may also be employed in the film.

Besides polymers, the elastic film may also contain other components as is known in the art. In one embodiment, for example, the elastic film contains a filler. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.; U.S. Pat. No. 6,461,457 to Taylor, et al.

The fillers may have a spherical or non-spherical shape with average particle sizes in the range of from about 0.1 to about 7 microns. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as stearic acid, may also be applied to the filler particles if desired. When utilized, the filler content may vary, such as from about 25 wt. % to about 75 wt. %, in some embodiments, from about 30 wt. % to about 70 wt. %, and in some embodiments, from about 40 wt. % to about 60 wt. % of the film.

Other additives may also be incorporated into the film, such as melt stabilizers, processing stabilizers, heat stabilizers, light stabilizers, antioxidants, heat aging stabilizers, whitening agents, antiblocking agents, bonding agents, tackifiers, viscosity modifiers, etc. Examples of suitable tackifier resins may include, for instance, hydrogenated hydrocarbon resins. REGALREZ™ hydrocarbon resins are examples of such hydrogenated hydrocarbon resins, and are available from Eastman Chemical. Other tackifiers are available from ExxonMobil under the ESCOREZ™ designation. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of films. Some suitable hindered phenols include those available from Ciba Specialty Chemicals of under the trade name "Irganox®", such as Irganox® 1076, 1010, or E 201. Moreover, bonding agents may also be added to the film to facilitate bonding of the film to additional materials (e.g., nonwoven web). When employed, such additives (e.g., tackifier, antioxidant, stabilizer, etc.) may each be present in an amount from about 0.001 wt. % to about 25 wt. %, in some embodiments, from about 0.005 wt. % to about 20 wt. %, and in some embodiments, from 0.01 wt. % to about 15 wt. % of the film.

The elastic film may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers, wherein the base layer is formed from a semi-crystalline polyolefin. In such embodiments, the skin layer(s) may be formed from any film-forming polymer. If desired, the skin layer(s) may contain a softer, lower melting polymer or polymer blend that renders the layer(s) more suitable as heat seal bonding layers for thermally bonding the film to a nonwoven web. For example, the skin layer(s) may be formed from an olefin polymer or blends thereof, such as described above. Additional film-forming polymers that may be suitable for use with the present invention, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

The thickness of the skin layer(s) is generally selected so as not to substantially impair the elastomeric properties of the film. To this end, each skin layer may separately comprise from about 0.5% to about 15% of the total thickness of the film, and in some embodiments from about 1% to about 10% of the total thickness of the film. For instance, each skin layer may have a thickness of from about 0.1 to about 10 micrometers, in some embodiments from about 0.5 to about 5 micrometers, and in some embodiments, from about 1 to about 2.5 micrometers. Likewise, the base layer may have a thickness of from about 1 to about 40 micrometers, in some embodiments from about 2 to about 25 micrometers, and in some embodiments, from about 5 to about 20 micrometers.

The properties of the resulting film may generally vary as desired. For instance, prior to stretching, the film typically has a basis weight of about 100 grams per square meter or less, and in some embodiments, from about 50 to about 75 grams per square meter. Upon stretching, the film typically has a basis weight of about 60 grams per square meter or less, and in some embodiments, from about 15 to about 35 grams per square meter. The stretched film may also have a total thickness of from about 1 to about 100 micrometers, in some embodiments, from about 10 to about 80 micrometers, and in some embodiments, from about 20 to about 60 micrometers.

III. Lamination Technique

The composite of the present invention is formed by laminating the nonwoven facing to the elastic film. Lamination may be accomplished using a variety of techniques, such as by adhesive bonding, thermal point bonding, ultrasonic bonding, etc. The particular bond pattern is not critical to the present invention. One suitable bond pattern, for instance, is known as an "S-weave" pattern and is described in U.S. Pat. No. 5,964,742 to McCormack, et al. Another suitable bonding pattern is known as the "rib-knit" pattern and is described in U.S. Pat. No. 5,620,779 to Levy, et al. Yet another suitable pattern is the "wire weave" pattern, which bond density of from about 200 to about 500 bond sites per square inch, and in some embodiments, from about 250 to about 350 bond sites per square inch. Of course, other bond patterns may also be used, such as described in U.S. Pat. No. 3,855,046 to Hansen et al.; U.S. Pat. No. 5,962,112 to Haynes et al.; U.S. Pat. No. 6,093,665 to Sayovitz et al.; D375,844 to Edwards, et al.; D428,267 to Romano et al.; and D390,708 to Brown. Furthermore, a bond pattern may also be employed that, similar to the spunbond web described above, contains bond regions that are generally oriented in the machine direction and have a size, aspect ratio, and/or arrangement such as described above. For example, the bond regions may have an aspect ratio of from about 2 to about 100, in some embodiments from about 4 to about 50, and in some embodiments, from about 5 to about 20.

Various embodiments of one suitable lamination technique will now be described in more detail. For example, the raw materials of the film (e.g., elastomeric polymer) may be initially dry mixed together (i.e., without a solvent) and added to a hopper (not shown) of an extrusion apparatus. The raw materials may alternatively be blended with a solvent. In the hopper, the materials are dispersively mixed in the melt and compounded using any known technique, such as batch and/or continuous compounding techniques that employ, for example, a Banbury mixer, Farrel continuous mixer, single screw extruder, twin screw extruder, etc.

Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al. For example, the compounded material can be supplied to the extrusion apparatus and then blown into nip rolls to form a single-layered precursor elastic film. The rolls may be kept at temperature sufficient to solidify and quench the precursor elastic film as it is formed, such as from about 20 to 60° C. If desired, the film may be stretched and thinned in the machine direction by passing it through a film-orientation unit or machine direction orienter ("MDO"), such as commercially available from Marshall and Willams, Co. of Providence, Rhode Island. The MDO may have a plurality of stretching rolls that progressively stretch and thin the film in the machine direction. The film may be stretched in either single or multiple discrete stretching operations. The film may also be stretched in other directions. For example, the film may be clamped at its lateral edges by chain clips and conveyed into a tenter oven. In the tenter oven, the film may be drawn in the cross-machine direction to the desired stretch ratio by chain clips diverged in their forward travel.

The nonwoven facing may be supplied from a supply roll or simply formed in-line. Although not necessarily required, a second nonwoven facing can also be laminated to the film, which may be a nonwoven facing as described herein (e.g., contains a necked spunbond web), as well as another type of nonwoven web material, film, foam, etc. As noted above, the spunbond web of the nonwoven facing(s) is necked. Such necking may occur prior to lamination. Alternatively, the spunbond web can be necked during lamination to the elastic film so that the resulting composite is considered "neck bonded." The elastic film may also be stretched, such as described above. If desired, such stretching may occur prior to lamination. Alternatively, the elastic film can be stretched during lamination to the nonwoven facing(s) so that the resulting composite is considered "stretch bonded." In yet other embodiments, the spunbond web of the nonwoven facing(s) can be necked and the elastic film can be stretched during lamination so that the resulting composite is considered "necked stretch bonded." Regardless, thermal bonding techniques may be employed to laminate the facing(s) to the elastic film.

For instance, the facing(s) may be directed to a nip defined between rolls for laminating to the elastic film. One or both of these rolls may contain a plurality of raised bonding elements and/or may be heated. Upon lamination, the elastic film is melt fused to the facing at a plurality of bond regions as described above.

Various additional potential processing and/or finishing steps known in the art, such as slitting, stretching, etc., may be performed without departing from the spirit and scope of the invention. It should be noted that due to its inherent cross-machine extensibility, the composite of the present invention need not be subjected to any additional post-formation procedures as is conventional. Nevertheless, such processes can be employed if so desired. For instance, the composite may optionally be mechanically stretched in the cross-machine and/or machine directions to enhance extensibility. In one embodiment, the composite may be coursed through two or more rolls that have grooves in the CD and/or MD directions. Such grooved satellite/anvil roll arrangements are described in U.S. Patent Application Publication Nos. 2004/0110442 to Rhim, et al. and 2006/0151914 to Gerndt, et al. Besides the above-described grooved rolls, other techniques may also be used to mechanically stretch the composite in one or more directions. For example, the composite may be passed through a tenter frame that stretches the composite. Such tenter frames are well known in the art and described, for instance, in U.S. Patent Application Publication No. 2004/0121687 to Morman, et al. The composite may also be necked. Suitable techniques necking techniques are described in U.S. Pat. Nos. 5,336,545, 5,226, 992, 4,981,747 and 4,965,122 to Morman, as well as U.S. Patent Application Publication No. 2004/0121687 to Morman, et al.

IV. Articles

The composite of the present invention may be used in a wide variety of applications. For example, as indicated above, the composite may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core. In one particular embodiment, the composite of the present invention may be used in providing a waist section, leg cuff/gasketing, ears, side panels, or an outer cover.

Figure 5:
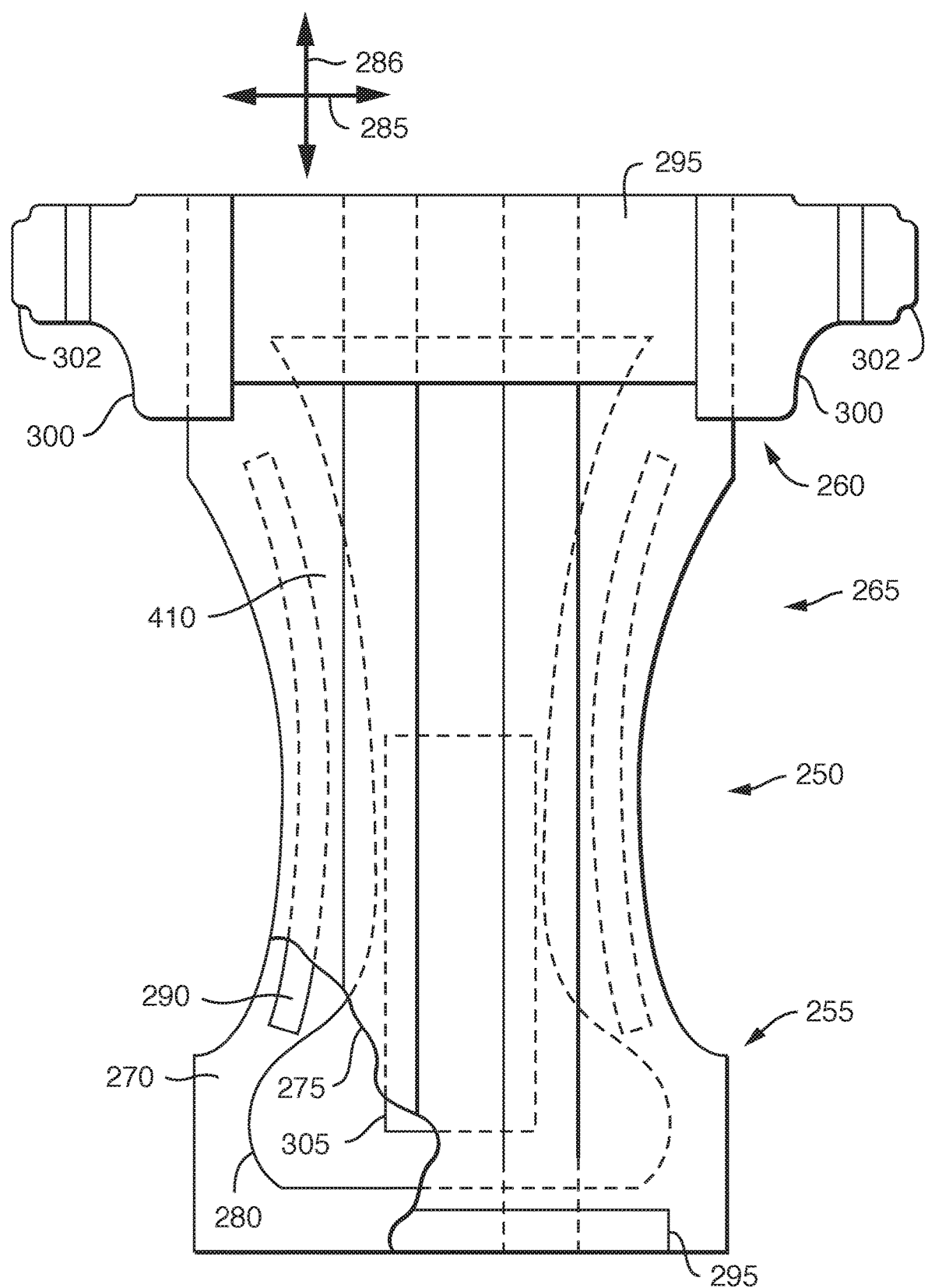
FIG. 5 is a perspective view of an absorbent article that may be formed in accordance with one embodiment of the present invention.

Various embodiments of an absorbent article that may be formed according to the present invention will now be described in more detail. Referring to FIG. 5, for example, one embodiment of a disposable diaper 250 is shown that generally defines a front waist section 255, a rear waist section 260, and an intermediate section 265 that interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area that is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 5, the diaper 250 may include leg elastics 290 constructed to operably tension the side margins of the diaper 250 to provide elasticized leg bands which can closely fit around the legs of the wearer to reduce leakage and provide improved comfort and appearance. Waist elastics 295 may also be employed to elasticize the end margins of the diaper 250 to provide elasticized waistbands. The waist elastics 295 are configured to provide a resilient, comfortably close fit around the waist of the wearer. The composite of the present invention may be suitable for use as the leg elastics 290 and/or waist elastics 295.

As is known, fasteners 302 (e.g., hook and loop fasteners, buttons, pins, snaps, adhesive tape fasteners, cohesives, fabric-and-loop fasteners, etc.) may be employed to secure the diaper 250 on a wearer. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may be elasticized or otherwise rendered elastic by use of the composite of the present invention.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 5, the disposable diaper 250 may also include a pair of containment flaps 410 which are configured to provide a barrier to the lateral flow of body exudates. The containment flaps 410 may be located along the laterally opposed side edges of the diaper adjacent the side edges of the liquid retention structure 280. Each containment flap 310 typically defines an unattached edge that is configured to maintain an upright, perpendicular configuration in at least the intermediate section 265 of the diaper 250 to form a seal against the wearers body. The containment flaps 410 may extend longitudinally along the entire length of the liquid retention structure 280 or may only extend partially along the length of the liquid retention structure. When the containment flaps 410 are shorter in length than the liquid retention structure 280, the containment flaps 410 can be selectively positioned anywhere along the side edges of the diaper 250 in the intermediate section 265. Such containment flaps 410 are generally well known to those skilled in the art. For example, suitable constructions and arrangements for containment flaps 410 are described in U.S. Pat. No. 4,704,116 to Enloe. Also, if desired, the containment flaps 410 may be elasticized or otherwise rendered elastic by use of the composite of the present invention.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the film of the present invention that may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al.; and U.S. Pat. No. 5,509,915 to Hanson et al.

The various regions and/or components of the diaper 250 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the topsheet 275 and backsheet 270 may be assembled to each other and to the liquid retention structure 280 with lines of adhesive, such as a hot melt, pressure-sensitive adhesive. Similarly, other diaper components, such as the elastic members 290 and 295, fastening members 302, and surge layer 305 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al. Further, other examples of personal care products that may incorporate such materials are training pants (such as in side panel materials) and feminine care products. By way of illustration only, training pants suitable for use with the present invention and various materials and methods for constructing the training pants are disclosed in U.S. Pat. No. 6,761,711 to Fletcher et al.; U.S. Pat. No. 4,940,464 to Van Gompel et al.; U.S. Pat. No. 5,766,389 to Brandon et al.; and U.S. Pat. No. 6,645,190 to Olson et al.

The present invention may be better understood with reference to the following examples.

Test Methods

Tensile Properties:

The strip tensile strength values were determined in substantial accordance with ASTM Standard D-5034. Specifically, a sample was cut or otherwise provided with size dimensions that measured 3 inches (76.2 millimeters) (width)×6 inches (152.4 millimeters)(length). A constant-rate-of-extension type of tensile tester was employed. The tensile testing system was a Sintech Tensile Tester, which is available from MTS Corp. of Eden Prairie, Minn. The tensile tester was equipped with TESTWORKS 4.08B software from MTS Corporation to support the testing. An appropriate load cell was selected so that the tested value fell within the range of 10-90% of the full scale load. The sample was held between grips having a front and back face measuring 1 inch (25.4 millimeters) ×3 inches (76 millimeters). The grip faces were rubberized, and the longer dimension of the grip was perpendicular to the direction of pull. The grip pressure was pneumatically maintained at a pressure of 60 to 80 pounds per square inch. The tensile test was run at a 20 inches per minute rate with a gauge length of 4 inches and a break sensitivity of 40%. Three samples were tested along the machine-direction ("MD") and three samples were tested by along the cross direction ("CD"). In addition, the ultimate tensile strength ("peak load"), and peak elongation was also recorded. The strength values may be initially reported as grams-force per 3 inches (sample width) and then normalized to grams-force per inch. Of course, other units may also be employed as is known in the art, such as Newtons per 5 centimeters or Newtons per centimeter.

Percent Set and Hysteresis

The materials were tested using a cyclical testing procedure to determine percent set. In particular, 1-cycle testing was utilized to 200% defined elongation. For this test, the sample size was 76.2 millimeters in the cross-machine direction by 152.4 millimeters in the machine direction. The grip size was 76.2 millimeters in width. The grip separation was 114.3 millimeters. A preload of approximately 10 to 15 grams was set. The test pulled the sample to 200% elongation at a speed of 508 millimeters per minute, and then immediately (without pause) returned to the zero at a speed of 508 millimeters per minute. The test reported percent set and percent hysteresis. The "percent set" is the measure of the amount of the material stretched from its original length after being cycled (the immediate deformation following the cycle test). The percent set is where the retraction curve of a cycle crosses the elongation axis. The remaining strain after the removal of the applied stress is measured as the percent set. The hysteresis value is the loss of energy during the cyclic loading. The testing was done on a MTS Corp. constant rate of extension tester 2/S with a Renew MTS mongoose box (controller) using TESTWORKS 4.07b software (MTS Corp, of Minneapolis, Minn.). The tests were conducted at ambient conditions.

Stress Relaxation

Stress relaxation testing may be performed by clamping a test specimen (76.2 millimeters in width) between the jaws of a MTS extension tester at a 76.2 millimeters grip to grip distance. The sample and the grip fixtures may be enclosed in an environmental chamber. The sample, after clamping, may be equilibrated at 37.8° C. for 3 minutes. The sample may then be elongated (e.g., in the cross-machine direction) to a final constant elongation of 152.4 millimeters (100% elongation) at a cross-head displacement speed of 508 millimeters per minute. The initial load required to maintain the 100% elongation may recorded as the "initial load." The load may also be monitored as a function of time and recorded. The "final load" may be the amount of force required to maintain the 100% elongation for 12 hours. The "percent load loss" may then be calculated by subtracting the final load (at 12 hours) from the initial load, dividing by the initial load, and then multiplying the ratio by 100.

The slope of the stress curve may also be reported. The slope, which may be constant over the time period, may be determined from a plot of log (load) versus log (time), or from the following equation:

$$m = \frac{-\Delta \log[L(t)/L(O)]}{\Delta \log t}$$

wherein, m=the slope,

L(t)=load at a given time (t),

L(0)=starting load at t=0, and t=time.

The testing may be done on a MTS Corp. constant rate of extension tester 2/S with a Renew MTS mongoose box (controller) using TESTWORKS 4.07b software (MTS Corp, of Minneapolis, Minn.).

COMPARATIVE EXAMPLE 1

A base spunbond web (target basis weight of 14-15 gsm) was formed from bicomponent core/sheath (70/30) filaments having a denier of 2. The core was formed from 100% polypropylene resin and the sheath contained 100% PE resin. The base spunbond web was bonded with raised pin calender rolls having a pattern such as shown in FIG. 2, where the pin area was 14% and the bonding temperature was 130-135° C. Once formed, the ratio of the machine direction tensile strength to the cross-machine direction tensile strength was determined to be 2.7. The base web was then necked from a starting width of about 81 centimeters to a necked width of 42 centimeters (i.e., 48% necking). Necking was performed by increasing the draw conditions on the web and simultaneously passing the web over a series of heated rolls in a temperature range of about 104-110° C. The draw ratio was 38% and held constant. The necked web was then laminated to an elastic film between an anvil and patterned roll with an oval shaped pin having an area of 0.0015 int and an aspect ratio of 2.38. The pins were oriented to 90 degrees with a pattern angle of 15 degrees and MD pin spacing of 0.093", leading to a total bond area of 11.0%.

EXAMPLE 1

A base spunbond web (target basis weight of 14-15 gsm) was formed from bicomponent core/sheath (70/30) filaments having a denier of 2. The core was formed from 100% polypropylene resin and the sheath contained 100% PE resin. The base spunbond web was bonded with raised pin calender rolls having a pattern such as shown in FIG. 2, where the pin area was 14% and the bonding temperature was 130-135° C. Once formed, the ratio of the machine direction tensile strength to the cross-machine direction tensile strength was determined to be 7.7. This ratio was achieved by adjusting the suction volume and corresponding air velocity through the forming wire in the forming section of the spunbond process. Filament diffuser settings and gaps were also used to promote the filament laydown in the machine direction. The base web was then necked from a starting width of about 81 centimeters to a necked width of 28 centimeters (i.e., 65% necking). Necking was performed by increasing the draw conditions on the web and simultaneously passing the web over a series of heated rolls in a temperature range of about 104-110° C. The draw ratio was 38% and held constant. The necked web was then laminated to an elastic film between an anvil and patterned roll with an oval shaped pin having an area of 0.0015 int and an aspect ratio of 2.38. The pins were oriented to 90 degrees with a pattern angle of 15 degrees and MD pin spacing of 0.093", leading to a total bond area of 11.0%.

Once formed, the composites of Comparative Example 1 and Example 1 were tested. The results are set forth below.

|  | Comparative Example 1 | Example 1 |
| --- | --- | --- |
| Load at 100% elongation ($g_f$ per 1" width sample) | 467 | 233 |
| % Elongation at 1400 $g_f$ | 110 | 225 |
| % Elongation at Peak Load | 190 | 350 |

While the invention has been described in detail with respect to the specific embodiments thereof, it will be appreciated that those skilled in the art, upon attaining an understandng of the foregoing, may readily conceive of alterations to, variations of, and equivalents to these embodiments. Accordingly, the scope of the present invention should be assessed as that of the appended claims and any equivalents thereto.

What is claimed is:

1. A nonwoven composite having a dimension in a machine direction and a cross-machine direction, the nonwoven composite comprising a nonwoven facing positioned adjacent to an elastic film, the nonwoven facing containing a necked spunbond web comprising a base spunbond web formed from a plurality of fibers that are generally oriented in the machine-direction, wherein the fibers contain a polymer composition that includes a fatty acid derivative, wherein the base spunbond web has a machine direction tensile strength and cross-machine direction tensile strength, the ratio of the machine direction tensile strength to the cross-machine direction tensile strength being 3:1 or more;

wherein the composite has a peak elongation in the cross-machine direction of 100% or more and experiences a load at 100% elongation in the cross-machine direction of 450 grams-force per inch (177.16 grams-force per centimeter) or less; and wherein the fibers are bonded together at multiple bond regions that are arranged in separate rows along the machine direction and spaced apart in the cross-machine direction within an individual row, wherein at least a portion of the bond regions are generally oriented in the machine direction.

2. The nonwoven composite of claim 1, wherein the composite exhibits a load loss of 60% or less in the cross-machine direction.

3. The nonwoven composite of claim 1, wherein the polymer composition includes a ductile polymer having a modulus of elasticity of 800 MPa or less as determined in accordance with ASTM D638-10.

4. The nonwoven composite of claim 3, wherein the fibers are bicomponent fibers containing a low modulus component that includes the ductile polymer.

5. The nonwoven composite of claim 3, wherein the fibers are monocomponent fibers.

6. The nonwoven composite of claim 3, wherein the ductile polymer is an ethylene polymer.

7. The nonwoven composite of claim 3, wherein the ductile polymer is a propylene homopolymer.

8. The nonwoven composite of claim 3, wherein the ductile polymer is a copolymer of propylene and an α-olefin.

9. The nonwoven composite of claim 3, wherein the polymer composition further contains a propylene homopolymer having a modulus of elasticity of from 800 MPa to 4,000 MPa as determined in accordance with ASTM D638-10.

10. The nonwoven composite of claim 1, wherein at least a portion of the bond regions have an aspect ratio of from 2 to 100.

11. The nonwoven composite of claim 1, wherein the elastic film contains a semi-crystalline polyolefin, a substantially amorphous block copolymer, or a combination thereof.

12. The nonwoven composite of claim 1, wherein the elastic film is laminated to the spunbond web at multiple bond regions, wherein at least a portion of the elastic film to spunbond web bond regions are generally oriented in the machine direction.

13. The nonwoven composite of claim 12, wherein at least a portion of the elastic film to spunbond web bond regions have an aspect ratio of from 2 to 100.

14. An absorbent article comprising the nonwoven composite of claim 1.

* * * * *